United States Patent

Lacroix

[11] Patent Number: 6,056,724
[45] Date of Patent: May 2, 2000

[54] DEVICE FOR INJECTION OF MEDICAL LIQUID

[75] Inventor: Jean-Pierre Lacroix, Annecy le Vieux, France

[73] Assignee: Medex, Annecy le Vieux, France

[21] Appl. No.: 09/002,768

[22] Filed: Jan. 5, 1998

[30] Foreign Application Priority Data

Jan. 6, 1997 [FR] France ................................. 97 00235

[51] Int. Cl.⁷ ........................... A61M 37/00; A61M 1/00
[52] U.S. Cl. ........................... 604/131; 604/141; 604/153
[58] Field of Search ............................. 604/131, 65, 132, 604/133, 141, 153, 257, 262; 222/103, 95; 128/DIG. 12, 205.15

[56] References Cited

U.S. PATENT DOCUMENTS

| | | | |
|---|---|---|---|
| 3,023,750 | 3/1962 | Baron | 128/214 |
| 3,199,511 | 8/1965 | Kulick | 128/214 |
| 3,507,278 | 4/1970 | Wenrding | 128/214 |
| 3,838,794 | 10/1974 | Cogley et al. | 222/95 |
| 4,270,533 | 6/1981 | Andreas | 128/DIG. 12 |
| 5,192,272 | 3/1993 | Faure | 604/141 |
| 5,700,245 | 12/1997 | Sancoff et al. | 604/145 |

FOREIGN PATENT DOCUMENTS 676 214 of 0000 European Pat. Off. .

*Primary Examiner*—Aaron J. Lewis
*Assistant Examiner*—Teena Mitchell
*Attorney, Agent, or Firm*—Fay, Sharpe, Fagan, Minnich & McKee, LLP

[57] ABSTRACT

A casing (20) includes a casing body (30) defined by a pair of lateral wall portions (32a, 32b) which are symmetric about a longitudinal plane (P) to define an ovoid transverse cross-section. The casing includes a lower fitting (35) that is connected with a source (23) of motive liquid (22) under pressure. A deformable enclosure (38) is sealed to an upper edge flange (41) of the casing. The deformable enclosure is drawn open (FIG. 9b) against a grid or cage (44) to receive a flexible pouch (18) that contains a medical liquid (19). A length of flexible tubing (17) connected to the pouch extends through a passage (37) in a cover or stopper (46) which is received on the casing body with a fluid tight seal. Under further motive fluid pressure, the flexible pouch (18) is squeezed, forcing the medical liquid through the tubing (17, 15, 9) to a cannula or other injection device (3).

19 Claims, 9 Drawing Sheets

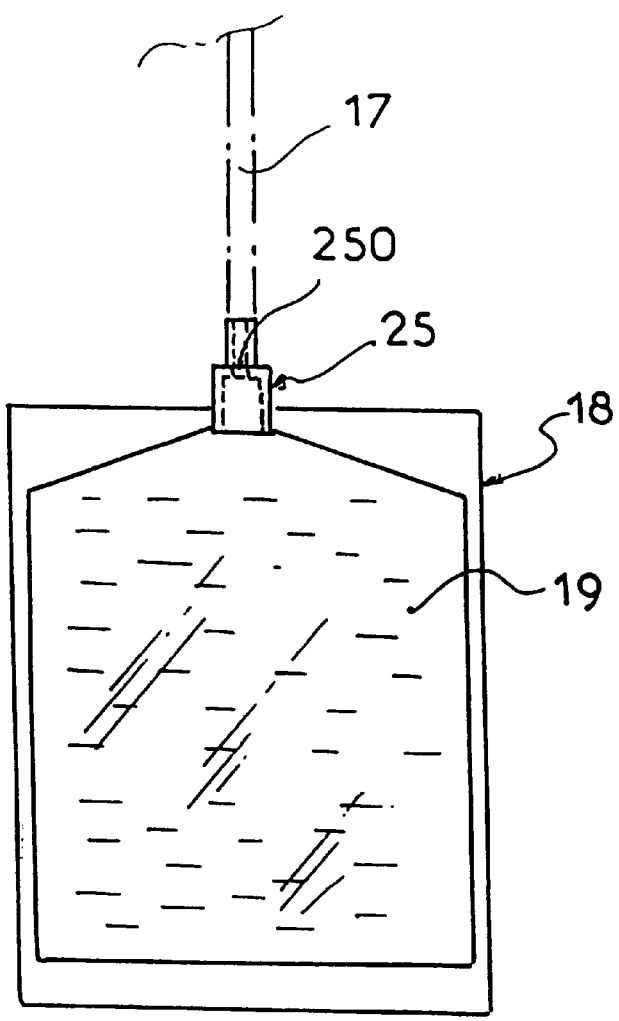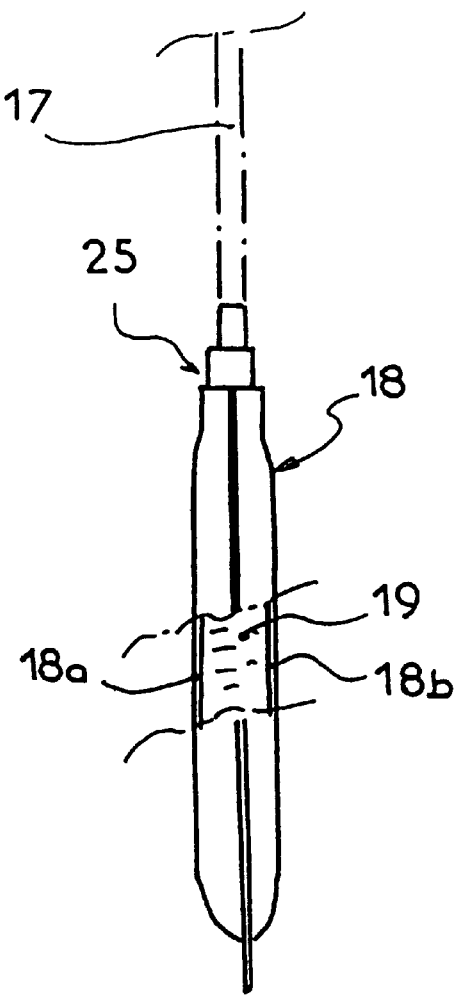

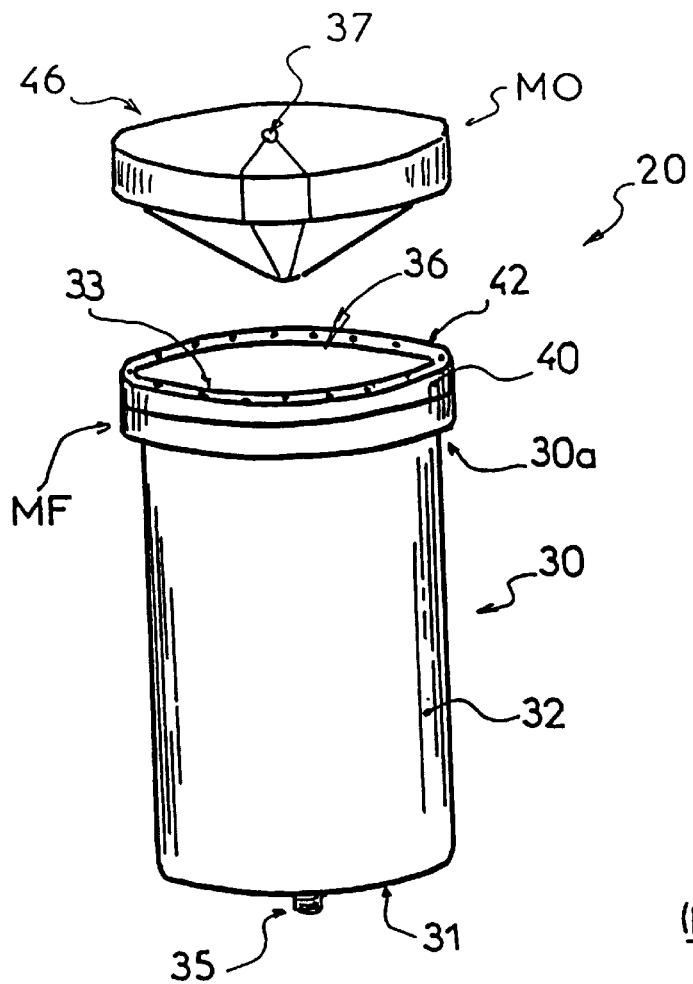
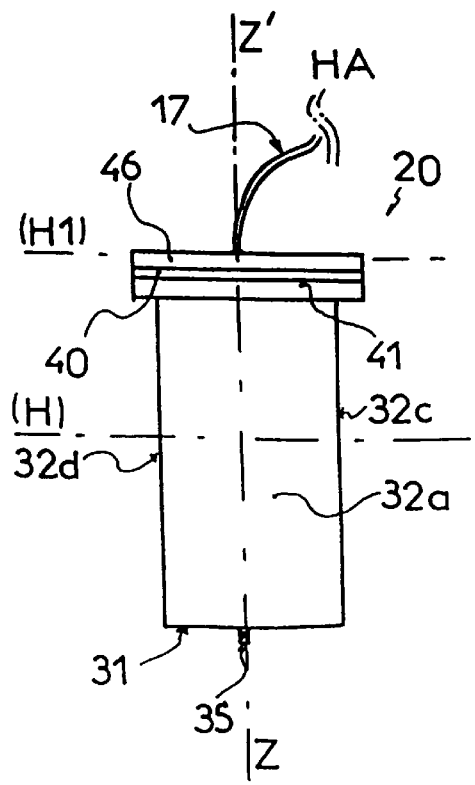

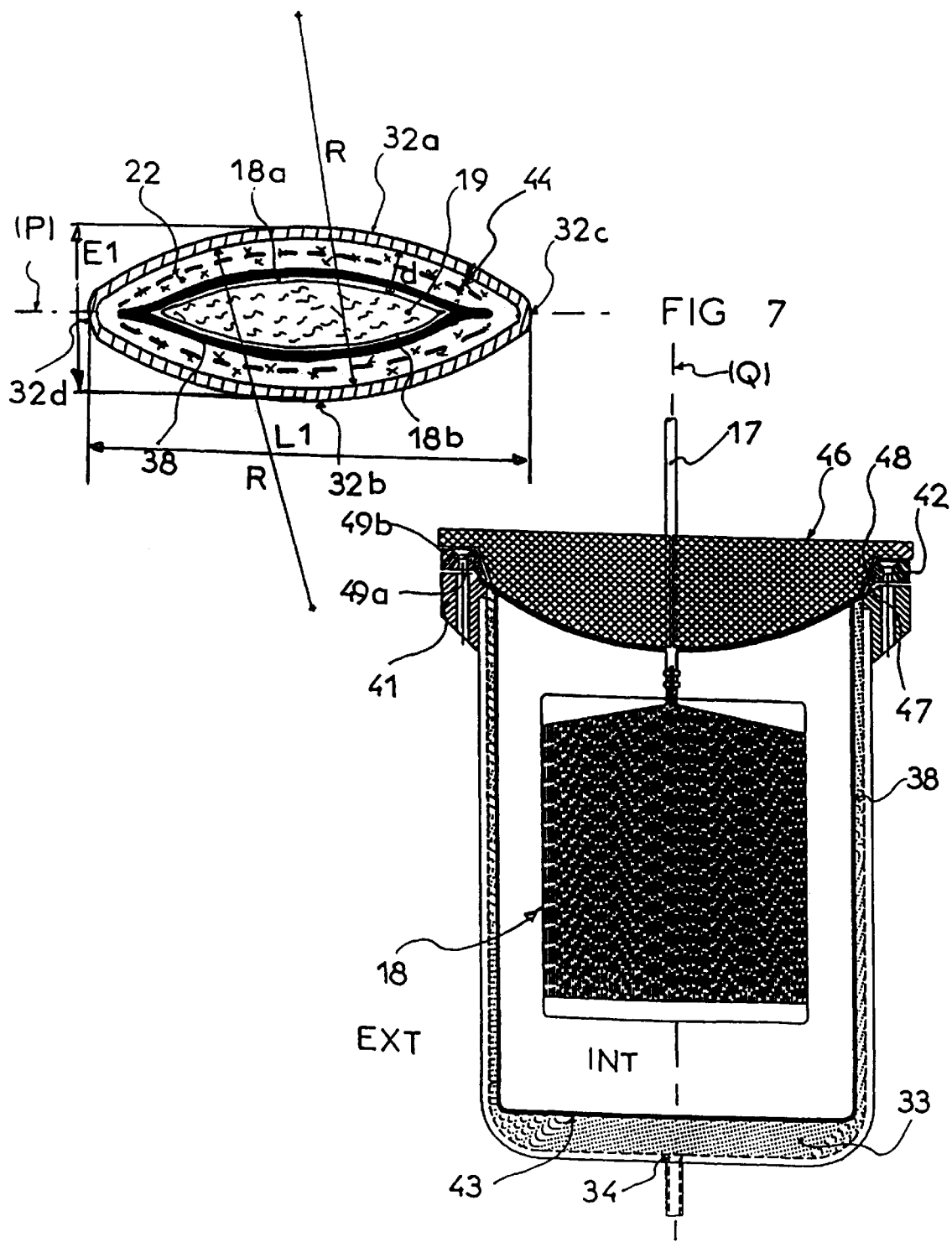

DEVICE FOR INJECTION OF MEDICAL LIQUID

BACKGROUND OF THE INVENTION

The present invention relates to the injection of pharmaceuticals and other medical liquids. It finds particular application in conjunction with human and veterinary injections. More specifically, it relates to an improvement in which the medical liquid is placed in a flexible envelope and injected under pressure.

Recent medical developments have resulted in new processes for analyzing and controlling the state of patients. Among these processes are analyses which are performed after injection of a contrast agent. Contrast agents may be used, for example, an angiographic analyses. In angiography, an iodine solution is injected into the vessels, veins, and arteries, in order to render them opaque to radiation and to impregnate tissues and organs with the opacifying substance. The contrast agent helps to emphasize and determine the presence of possible thromboses, embolisms, compressions, and other abnormalities in radiographic images.

Contrast products are also used in scanning procedures or during traditional or digital angiography. The contrast agent is injected into the vein or artery at rates ranging generally from 0.5 to 35 ml/sec. to form a bolus of the contrast agent moving through the veins or arteries. There are, however, alternate types of injections other than injections of contrast agents, such as transfusions, procedures for artificial nutrition by blood or by digestive route (enteral or parenteral).

Prior injection devices include syringes including the liquid to be injected. The syringe has an injection head which is connected to a hypodermic or intravenous needle or to a catheter by interconnecting flexible tubing. Often, the tubing includes an anti-retention threshold valve. Conventional syringes are prepared by filling and air removal from flasks of different contents, such as 60, 100, 200 ml, or even 500 ml. In view of the increasing requirements in areas of hygiene and with respect to patients, it is desirable to deliver a non-contaminated product to several patients. It is desirable to avoid, to the greatest degree possible, any decantation from flask to syringe, particularly if the syringes are destined to serve several patients. This avoids any risk of retrograde contamination by drawing fluids from a patient back into the syringe. The development of contagious diseases, specifically the development of the AIDS disease, has motivated physicians to increase requirements in the area of hygiene. It is thus a determining factor and extremely important to suppress all risks of contamination and avoid, to the maximum extent possible, decantations of initially required products and to do so primarily for purposes of hygiene and safety. Thus, devices have been conceived in which the medical liquid is stored in packaging which includes a flexible pouch fitting with a coupling. The pouch replaces the traditional syringe. The pouch coupling is connected to tubing which is linked to an injection conduit, such as a catheter or hypodermic needle, intravenous or other. The flexible pouch is placed in a casing that includes an inert motive liquid which is placed under pressure.

Such devices are described, for example, in European Patent Application Nos. 0 343 286 and 0 676 214, in U.S. Pat. No. 3,199,511, as well as in French Patent Application No. 2,592,306. In all of these devices, a flexible pouch contains the liquid to be injected. The pouch is placed in an enclosure containing the motive liquid which is placed under pressure to propel the liquid contents from the pouch. These devices, however, present drawbacks in their modes of utilization and construction. In fact, certain devices are not very practical for users, specifically when changing the flexible pouch or ridding the pouch bubbles. Additionally, in some instruments, the pressure distribution over the pouch is unsatisfactory, decreasing accuracy of regulation of the injection parameters. This is due in part to the flexible pouch gradually changing in flexibility or shape with use. Furthermore, all of these devices are intended only to performing perfusions and in no case are they held out as suitable for the injection of contrast agents.

The present invention proposes a simple, new device which overcomes the above-referenced problems, yet is easy to use, reliable, and accurate.

SUMMARY OF THE INVENTION

In accordance with one aspect of the present invention, a device is provided for the injection of medical liquids. A flexible pouch contains the medical liquid to be injected. The pouch is tight and comprises at least one outlet opening for connection to tubing linked to an injection conduit, such as a catheter or a hypodermic, intravenous, or other needle. The flexible pouch is deformed by an inert motive liquid which is placed under pressure in such a manner that it transmits the pressure to the medical liquid to be injected. By placing the flexible pouch in a casing containing the motive liquid and putting it under pressure, the motive liquid is forced to issue into the tubing. The casing has a longitudinal, general plane of symmetry. The casing includes a casing body having an upper opening located at an upper end and a movable sealing means which is movable between an open position to receive the flexible pouch and a sealed position closing the casing. The casing body has a transverse section of a generally oval shape, such as egg-shaped, oblong, or elliptical. The casing body has a lower end wall and a peripheral wall formed by at least two lateral wall portions of curved shape.

In accordance with a more specific embodiment, the lateral wall portions each have a transverse section of generally circular shape. The generally circular wall portions are non-concentric and have identical radius. The radius of the transverse section of the lateral wall portions is constant along the longitudinal axis of the casing body.

The casing includes a deformable enclosure arranged in the interior of the casing body. The deformable enclosure is formed by two flexible plane walls extending in an upward direction by a divergent wall.

Furthermore, a positioning means is provided to permit the deformable enclosure to be positioned generally in the longitudinal plane of symmetry of the casing.

According to another variation, the device includes a means for shaping the deformable enclosure to permit the enclosure to take on the approximate shape of a filled flexible pouch before the flexible pouch is inserted. The shaping means includes guide bars arranged around the deformable enclosure in such a manner that the deformable enclosure is positioned and shaped into a form approximately identical to the form of the flexible pouch.

According to a preferred embodiment of the invention, the sealing means includes a passage opening which permits connection of the flexible pouch to the tubing. The sealing means is formed by a lid including two complementary parts that are movable relative to each other.

According to a complementary characteristic, a plane of general longitudinal symmetry of the casing is arranged substantially vertical with the upper opening of the casing body oriented towards the top. In this manner, the evacuation of air bubbles which might potentially be retained in the pouch is permitted.

One advantage of the present invention is that it is usable with any of a variety of types and sizes of flexible pouches. Preferably, pouches from 50 to 500 ml can be accommodated.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 2 is a front view of a deformable pouch for holding medical liquid in the system of FIG. 1;

FIG. 3 is a side view of the pouch of FIG. 2 in partial section;

FIG. 4 is a perspective view of a casing body and sealing means of the system of FIG. 1;

FIG. 5 is a side view of the casing body of FIG. 4;

FIG. 6 is a transverse sectional view of the casing body through Section H of FIG. 5;

FIG. 7 is a longitudinal sectional view along Section P of FIG. 6 of the casing body and an enclosed flexible pouch;

FIG. 8b is a side view of the deformable enclosure of FIG. 8a;

FIG. 8c is front view of the flexible enclosure of FIG. 8a;

FIG. 8d is a top view of the flexible enclosure of FIG. 8a;

DETAILED DESCRIPTION OF THE PREFERRED EMBODIMENTS

Figure 1:
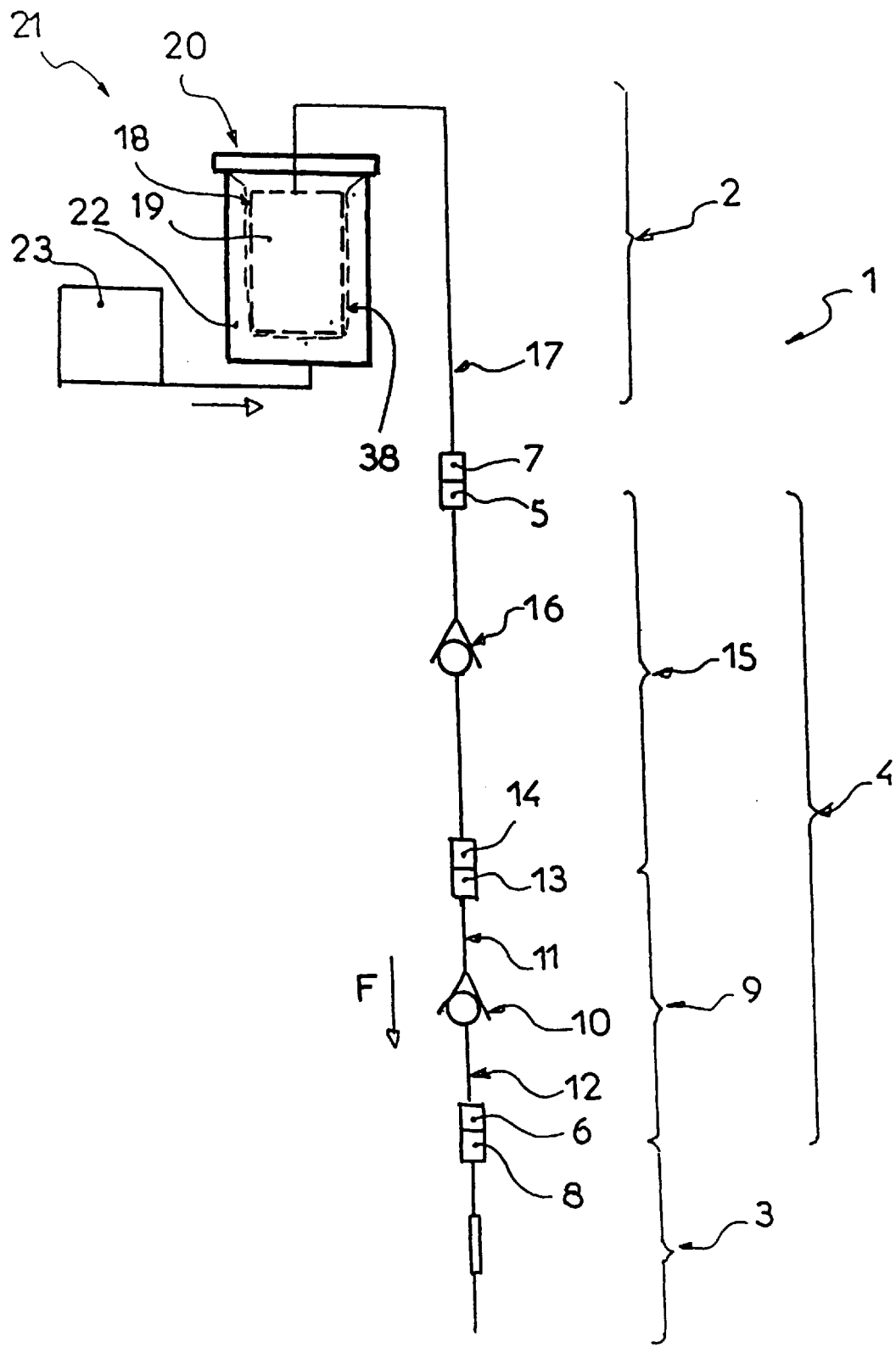
FIG. 1 is a schematic diagram of a preferred embodiment of an injection device in accordance with the present invention.

With reference to FIG. 1, an injection device 1 includes an injected liquid supply device 2 connected to an injection conduit or cannula 3, such as a catheter, hypodermic or intravenous needle, by intermediate tubing 4. The intermediate tubing 4 has an upstream coupling 5 and a downstream coupling 6. The upstream coupling 5 is connected to a supply coupling 7 of the injector or supply device 2. The downstream coupling 6 is connected with an upstream coupling 8 of the injection conduit 3. Preferably, the intermediate tubing 4 includes a safety device 9 such as a no-return check valve 10 connected between upstream tubing 11 and downstream tubing 12. A suitable safety device is described in French Patent Application No. 93 12590. The no-return check valve is adjusted to permit liquid to pass from upstream to downstream as indicated by flow arrow F under positive pressure in excess of a preselected threshold pressure. The check valve blocks the passage of liquid in an opposite direction, i.e., from downstream to upstream, in a direction opposite to arrow F. It should be noted that the upstream tubing 11 of the safety device 9 is connected with an upstream coupling 13 which is connected to a downstream coupling 14 of an upstream portion 15 of the intermediary tubing 4. The upstream portion 15 includes another no-return check valve 16. The downstream tubing 12 includes the previously described downstream coupling 6.

The intermediary tubing 4 is connected to the injector or supply device 2 by the upstream coupling 5 which is connected to the coupling 7. The coupling 7 is connected directly to the end of a supply conduit 17 of a flexible pouch 18 containing the medical liquid 19 to be injected. The flexible pouch 18 is arranged in a pressurize casing 20 of a pressurized device 21 of the injector 2. The flexible pouch is pressurized by a surrounding, inert motive liquid 22. The inert motive liquid 22 is contained in the casing 20 and is pressurized by a pressuring means 23, such as a high pressure pump, e.g., a sliding piston pump driven by a controlled electrical motor or other such motorized or manual devices.

With reference to FIGS. 2 and 3, the flexible pouch 18 contains the medical liquid 19 to be injected. The couch is formed of two sheets of flexible plastic material. The first sheet 18a and an identical second sheet 18b are joined peripherally by gluing, welding, or the like, to define an internal volume that contains the medical liquid 19. Further, the lower portion of the flexible pouch includes a discharge tube 25 which is temporarily sealed by a membrane 250 during shipping and handling which is pierced during interconnection with the supply conduit 17. Alternately, the pouch may include an integral supply conduit 17 as illustrated in phantom. The liquid containing pouch is soft and deformable. When put in a place in which it is totally surrounded by the motive liquid 22 and put under pressure, the pouch deforms in a homogeneous and peripheral fashion forcing the medical liquid to discharge into the tubing 4.

With reference to FIGS. 4–7, in the preferred embodiment, a casing body 30 has a generally longitudinal plane of symmetry P (FIG. 6). The casing body has a lower end wall 31 and a peripheral wall 32 which define an internal enclosure 33 which contains the inert motive liquid 22. The casing body 30 includes a coupling device 34 for connection to a pressurizing means 23 of the injection device 1 with motive liquid 22 received in the enclosure 33. The coupling orifice 34 is preferably situated in the lower end wall 31 and is equipped with a cylindrical wall extension 35 which is preferably threaded and extends to the exterior (EXT) in order to facilitate connections. Of course, the connection means between the casing body 30, more specifically between the extension 35 and the pressuring means 23, can be of any other known type.

The casing body 30 includes an upper end 30a which defines an upper opening 36 to permit introduction of the flexible pouch 18 containing the medical liquid 19. A sealing means MO for the opening 36 of the casing body is movable between an open position which permits introduction of the flexible pouch and a closed position in which the enclosure is closed. The sealing means MO preferably includes a passage 37 through which the supply conduit 17 and/or a portion of the discharge tube 25 is permitted to pass therethrough for interconnection with the flexible pouch. In this manner, the tubing 4 is interconnected with the flexible pouch when the flexible pouch is disposed in the interior INT of the internal closure 33 of the casing 20.

In the preferred embodiment, the lateral peripheral wall 32 of the casing body 30 presents an elongated transverse section of oval or egg-like shape in a transverse plane H perpendicular to the plane of symmetry P. In the preferred embodiment, the peripheral wall has two lateral wall portions 32a, 32b of curved shape rounded toward the exterior of the disclosure. Preferably, the rounded section extends along a circular arc segment in the transverse plane H. The two circular arc segments are non-concentric, but have an identical radius R, preferably between 10 and 18 cm, more preferably approximately 14 cm.

With particular reference to FIGS. 5 and 6, the lateral wall portions 32a, 32b are symmetrically arranged on opposite sides of the longitudinal plane P and are, for example, connected to each other by two longitudinal welding strips 32c, 32d in the form of two curved wall portions whose radius of curvature in the transverse plane H is small.

In the preferred embodiment, the casing body 30 has a transverse section of oblong shape, laterally curved, whose shape and dimensions are approximately constant along the longitudinal axis Z,Z' of the casing. The radius R of the peripheral walls 32a, 32b will vary in accordance with the longitudinal axis Z,Z' without extending beyond the present invention. Thus, when a filled flexible pouch 18 is introduced into the closure 33, the oval shape of the transverse section of the casing body 30 allows a distance D between the peripheral wall portions 32a, 32b of said body in the walls 18a, 18b of the pouch to be approximately constant in the transverse plane.

In the preferred embodiment, a deformable enclosure 38 for receiving the flexible pouch 18 lines the interior INT of the internal closure 33 from the upper opening 36 located at the upper edge 30a. The deformable enclosure is hermetically sealed approximately at the level of the upper opening 36 at the interior of the internal enclosure 33 by a sealing or fixation means MF so as to accommodate the flexible pouch 18 in its interior without the flexible pouch being in direct contact with the internal motive liquid 22.

Figure 8A:
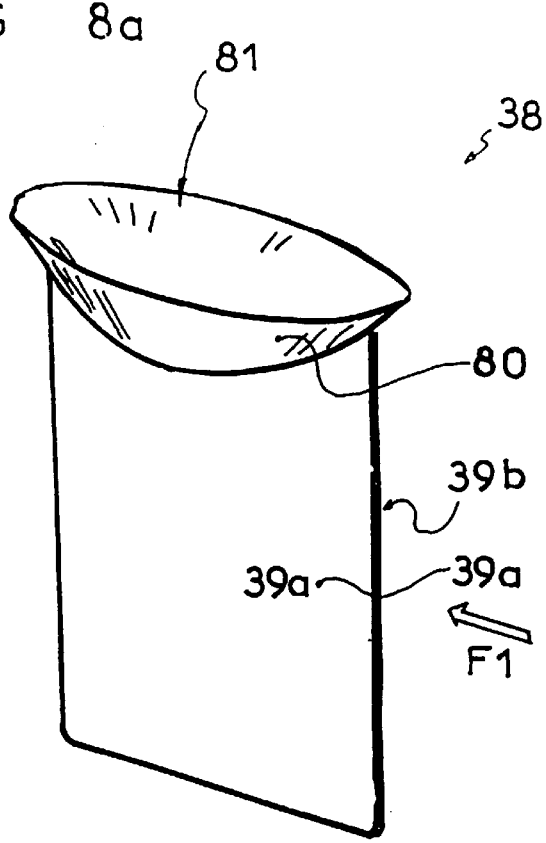
FIG. 8a is a perspective view of a deformable enclosure which is disposed in the casing body to receive the flexible pouch.
Figure 8B:
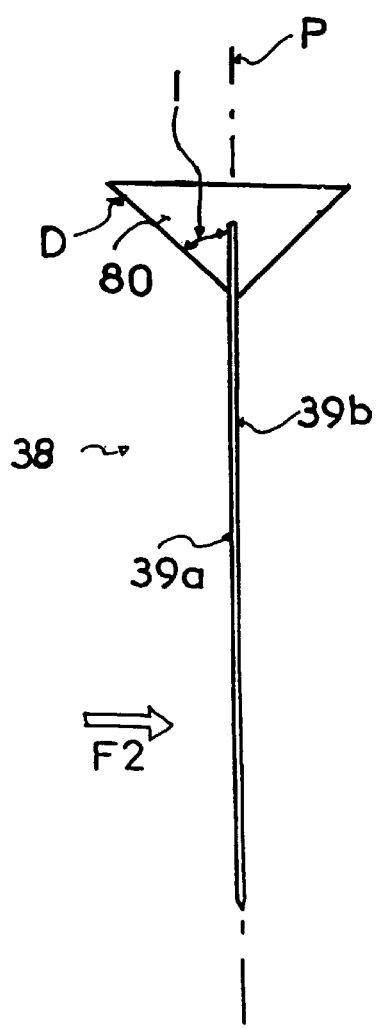
Figure 8C:
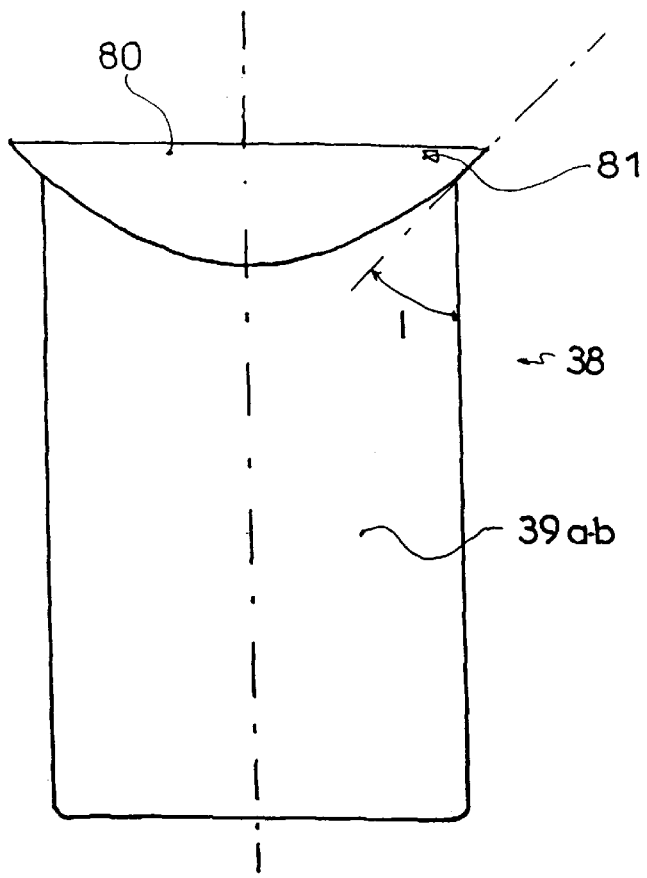
Figure 8D:
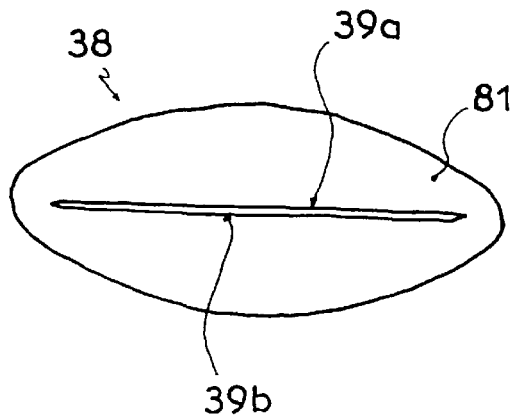

With reference to FIGS. 8a–8d, the deformable enclosure 38 is defined by two deformable flexible walls 39a, 39b whose lateral and lower edges are hermetically sealed. The deformable closure has a divergent wall 80 toward its top whose upper edges 81 are hermetically sealed by the fixation means MF to the periphery of the upper opening 36. This permits the flexible pouch to be received in the deformable enclosure 38. The divergent wall 80 is defined by a surface extending at an angle I of about 45° relative to the vertical plane. The divergent wall in the transverse plane H is an elongated oval or egg-shape which corresponds to the elongated oval or egg-shaped form of the lateral peripheral wall 32 and sized to meet or exceed the size of the upper opening 36. The shape of the divergent wall 80 may be rounded at its lower portion along the longitudinal plane as depicted in FIG. 8c. With reference again to FIG. 5, the fixation means MF includes a fixation device 40 defined by cooperation between an upper edge 41 of the casing body 30 which is flared out towards the exterior of the body in a transverse plane H1 which is located approximately at the level of the upper opening 36. Upper edges 81 of the divergent wall 80 of the flexible walls 39a, 39b is wedged between the flared edges 41, 46. The divergent wall 80 thus forms a tight joint. The mounting flange 40 is fixed against the edge 41 with a mechanical connector, such as a screw 42, rivets, or the like. The wedging of the flexible walls is preferably done along a chamfer of the opening 36 of the casing body and a complementary chamfered surface 48 of the fixation device 40, leaving the opening unencumbered as illustrated in FIG. 7. Of course, other constructions for fixing the deformable enclosure 38 to the casing body 30 are contemplated.

In the preferred embodiment, the deformable enclosure 38 is constructed of a flexible and deformable material such as latex, neoprene, silicon, or polydimethyl elastomer.

Further, the injection device 1 includes a positioning means for the deformable enclosure 38 which positions the deformable enclosure such that it extends approximately in the plane P and such that it keeps the flexible pouch 18 in the plane P. In the preferred embodiment, the positioning means includes a metal edge or rod which is integral with the lower edge 43 of the deformable enclosure. The metal element is maintained in the plane P by a rigid connection means which connects it, for example, to the lower end wall or by a semirigid connection means which permits a small amount of longitudinal play.

With reference to FIGS. 9a–9d, a shaping means MMF facilitates introduction of the flexible pouch 18 into the interior of the deformable enclosure 38 and permits the deformable enclosure to assume a shape which substantially matches the shape of the filled flexible pouch. The shaping means MMF preferably includes guide bars or a rigid grid 44 whose shape corresponds to the filled flexible pouch 18. The grid 44 extends around the deformable enclosure 38. The shaping means MMF permits the flexible walls 39a, 39b of the deformable enclosure to move apart from each other against the grill 44 providing for easy access into the enclosure 38. In this manner, the flexible enclosure approximately takes on the shape of the filled flexible pouch facilitating its receipt. It is to be understood that the shaping means MMF may be embodied in numerous other physical constructions which achieve the same purpose and perform the same or a similar function.

Figure 10:
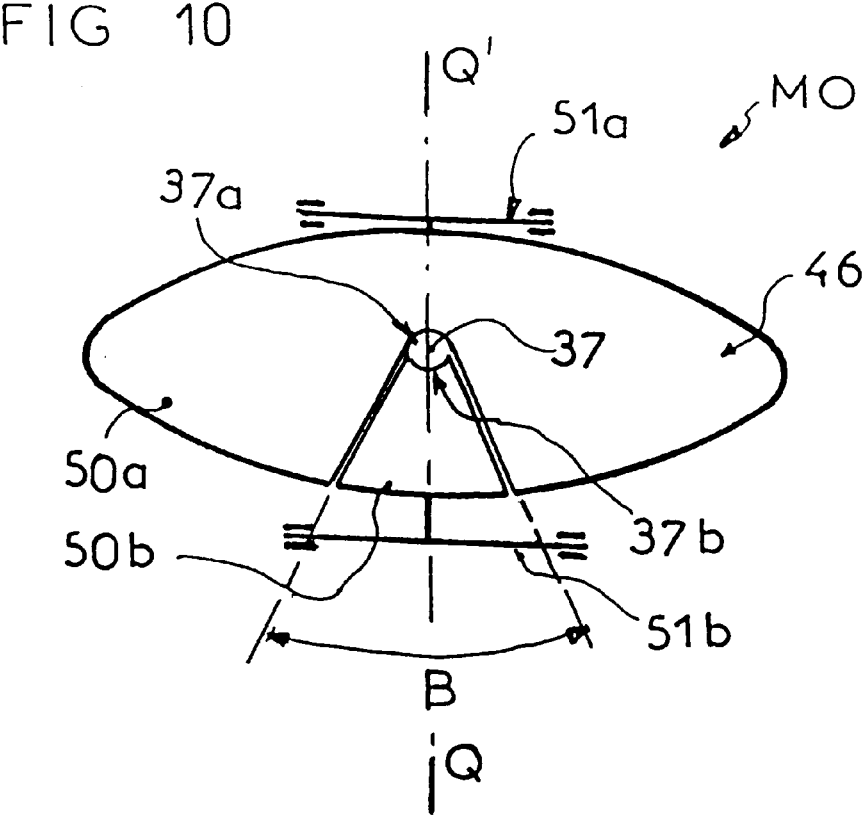
FIG. 10 is a top schematic view of the lid or stopper of the casing body.
Figure 11:
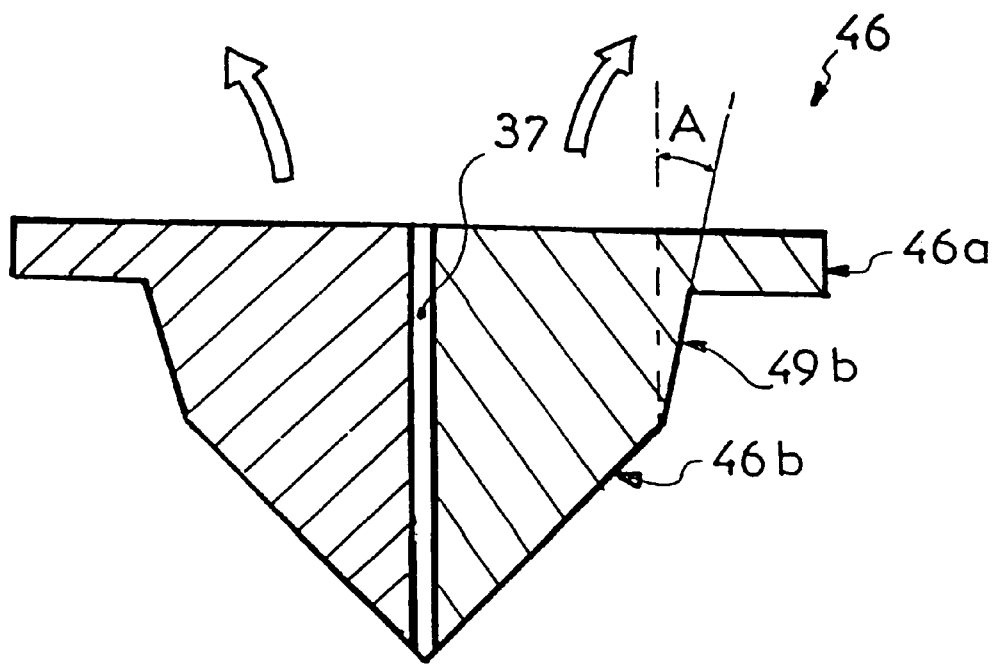
FIG. 11 is a sectional view of the stopper of FIG. 10 along section Q–Q'.

With reference to FIGS. 10 and 11, in accordance with the preferred embodiment, the sealing means MO of the internal enclosure 33 includes a detachable stopper or lid 46. The lid 46 includes an upper plate 46a, whose form and dimensions are preferably identical with the contour of the upper surface 46 of the fixation device 40. The upper plate 46a is extended towards the bottom by a projection 46b whose section in the transverse plane presents an elongated oval or egg-shaped form complementary to that of the inner surface of the peripheral wall 32. The upper plate projection and the upper opening have a tight clearance in the transverse plane in order to provide the hermetic seal to the internal enclosure 33.

The dimensions of the transverse section of the stopper or lid 46 progressively decrease in the lower portion of the projection 36b in such a manner as to follow the flared shape of the divergent wall 80 of the deformable enclosure 38.

In accordance with the present invention, the lower projection 46b of the stopper has the elongated oval or egg-shaped form in transverse section and at its bottom-most edge tapers at approximately 45° so as to match the shape of the upper extension 80 of the flexible envelope. In the preferred embodiment, the upper opening 36 and the stopper lower projection 46b have cooperating chamfers 49a on the upper opening and 49b on the stopper, such that they engage in a cooperative relationship. Preferably, the chamfer is inclined at an angle A of about 15°. The shape and size of the lowermost stopper portion 46b are selected such that it cooperates in a tight, complementary fit with the divergent wall 80 of the deformable enclosure.

Further, the orifice passage 37 of the sealing means MO is preferably defined by a passage or channel at the center of the stopper 46. In the preferred embodiment, the stopper is constructed of two portions 50a, 50b. The complementary portions cooperatively mate such that two complementary grooves 37a, 37b, one in each of the stopper portions, define the passage 37. In this manner, the two stopper portions are separable to permit placement of the supply conduit 17 and/or a portion of the discharge tube 25 into one of the grooves when the two parts are separated. In the preferred embodiment, part 50b is a sector centered on the axis Z,Z' and diverges at an angle B, preferably between 10° and 90°. The two parts 50a, 50b are preferably articulated in relationship to the casing body 30 by two hinge type articulations 51a, 51b between the open portion of the stopper 46 and the sealed position of the enclosure, as illustrated schematically in FIG. 10. A locking means locks the lid 46 on the casing body 30 in order to permit pressurizing of the inert motive liquid 22 in the interior of the enclosure 33 when the lid hermetically seals the opening 36. The casing body 30 is preferably constructed of aluminum or steel in order to withstand a pressure in the range of 80 to 100 bars. The inert motive liquid is preferably water, glycerine, or a mixture of the two.

In order to facilitate the removal of air bubbles, which are undesired, the flexible pouch 18 and the casing 20 are oriented with the discharge orifice of the pouch connected to the outlet tubing along the longitudinal axis Z,Z' in an upward direction HA. The upper opening 36 of the casing body is located at the upper end.

Figure 12:
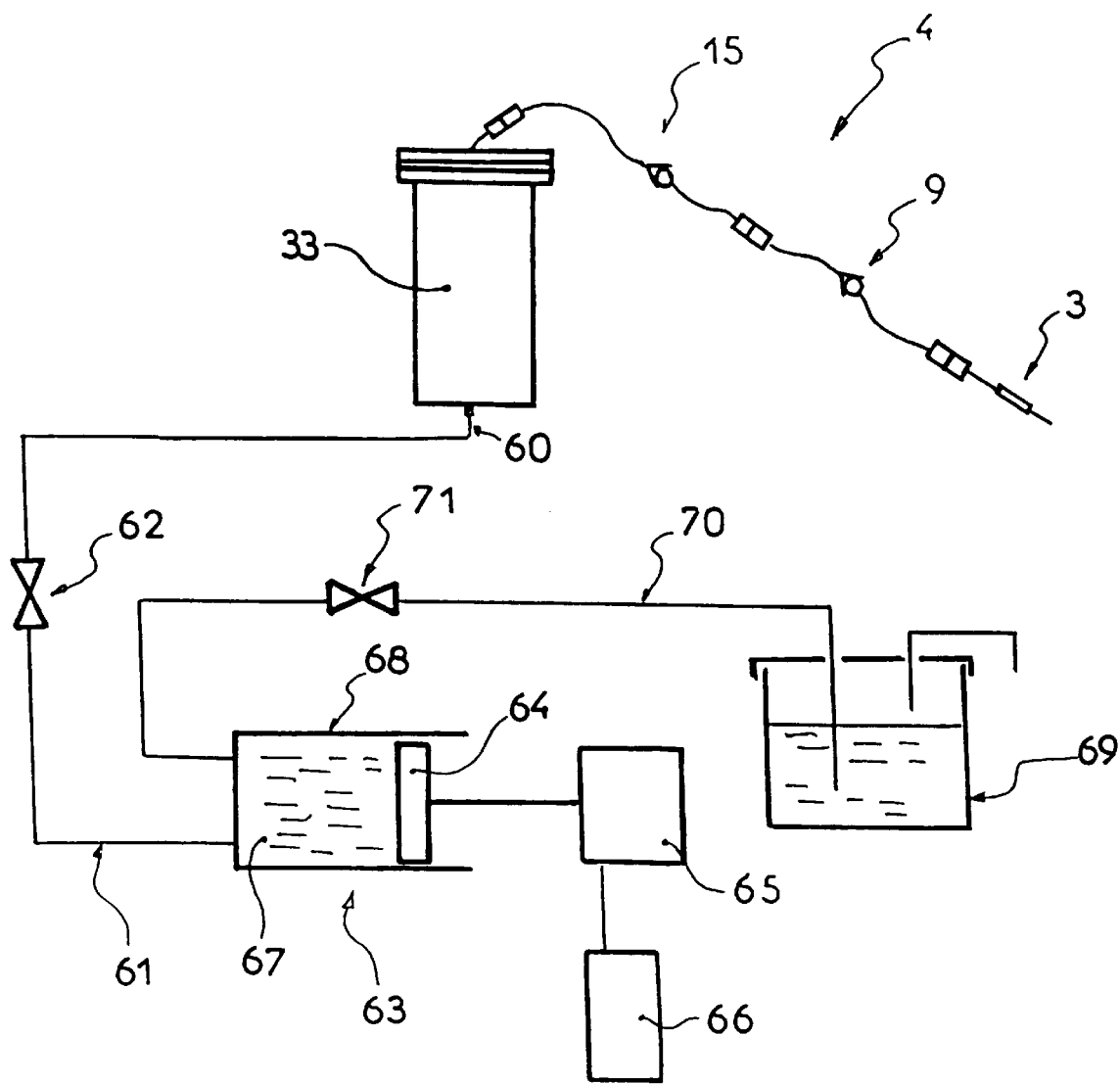
FIG. 12 is a diagrammatic illustration of an injection system in accordance with the present invention.

With reference to FIG. 12, the enclosure 33 is fed with a pipe 61. The pipe 61 includes a main, electrically controlled shut-off valve 62. The pipe 61 is connected to a piston pump 63 whose piston 64 is driven by an electrical motor 65 controlled by an automatic control mechanism 66.

More specifically, the piston pump 63 has a chamber 67 defined between the piston and a cylinder 68 which is connected to a motive liquid reservoir 69 by a second conduit 70. A second electrical shut-off valve 71 is defined in the second conduit.

During a preliminary phase, the device is reset to zero. The enclosure 33 is closed by the sealing means MO without having put the pouch of liquid to be injected in place. With the shut off valve 62, 71 open, the piston 64 is retracted. The shut-off valve 71 is then closed and the position of the piston is marked as the zero setting.

Figure 9A:
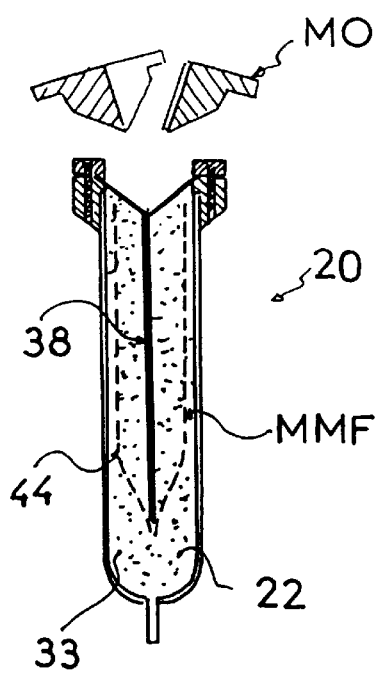
FIG. 9a is a cross sectional view of the casing body and flexible enclosure taken along section plane Q of FIG. 7 in an initial position.
Figure 9B:
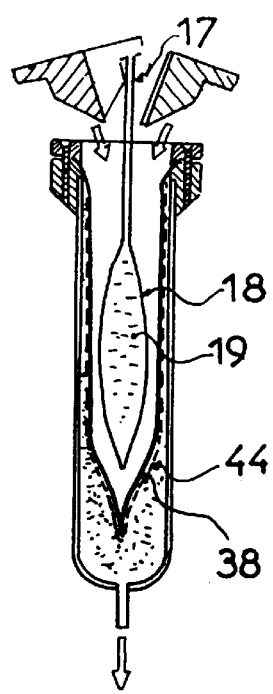
FIG. 9b is the same cross-section as FIG. 9a, but with the deformable enclosure expanded to receive the flexible pouch.

In the next phase, as illustrated in FIGS. 9a and 9b, the flexible pouch is introduced into the casing 20. During this phase, the device is placed under negative pressure withdrawing the enclosure 33 and displacing a portion of the motive liquid 22 contained therein. As a result, the flexible walls 39a, 39b of the deformable enclosure take on the form of a filled flexible couch due to the shaping means MMF. The flexible pouch 18 is then introduced into the deformable enclosure and the supply passage 17 is positioned in the orifice 37 of the sealing means MO. The sealing means is then sealed into position.

Figure 9C:
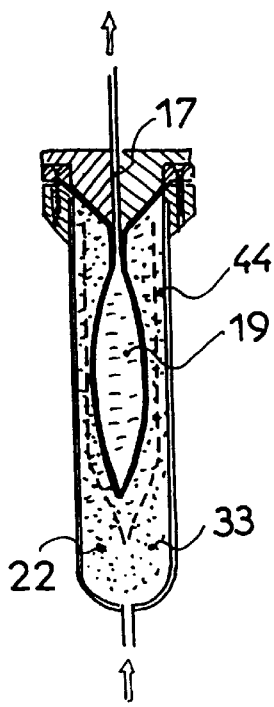
FIG. 9c is the same cross-section as FIG. 9a, but with the casing closed at the initiation of the injection phase.
Figure 9D:
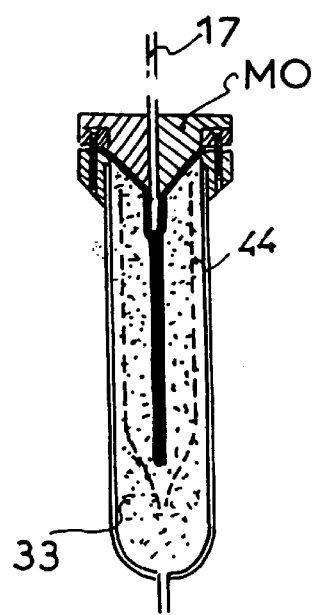
FIG. 9d is the same cross-section as FIG. 9a at the end of the injection phase.

As illustrated in FIG. 9c, in the injection phase, the motive liquid 22 is reintroduced into the interior of the enclosure 33. More specifically, the motive liquid is introduced with a preselected pressure causing deformation of the flexible pouch 18. The deformation provokes a discharge of the medical liquid through the tubing 4 and the supply passage 17. With reference to FIG. 9d, when the flexible pouch is empty, injection is terminated. The exertion of pressure on the motive liquid in the interior of the enclosure 33 is terminated to permit the sealing means MO to be opened and an the empty flexible pouch replaced with a full pouch. The procedure can then be recommenced with the new pouch as described above.

Of course, it is to be understood that other mechanisms for pressurizing may be utilized, and that such other mechanisms may be either motorized or manual.

Similarly, various control mechanisms and algorithms to manage the flow rates of the medical liquid either automatically, semiautomatically, or manually, are contemplated. Beneficially, the volume variations and rate variations are constantly controlled by the control means 66 in order to ensure accurate and safe injections.

Optionally, a safety system is provided which prevents injections when the casing body is open. Furthermore, it is to be understood that the device is preferably supported on a support, either movable or fixed, which is supported on the ground or suspended from a gantry, or even attached to a ceiling or wall. The support may also include a control or monitoring table.

It is to be understood that the casing body can have any shape of elongated transverse section with a width L1 which is greater than a thickness E1. The casing may be made out of any material such as, for example, steel, stainless steel, aluminum, or plastic materials. Further, the casing may be constructed by flattening or deforming a cylindrical tube.

Of course, means may be provided for retaining the low profile of the deformable enclosure in such a manner as to block it from setting up in an untimely fashion.

Further, the size of the casing may vary to hold any of several sizes of injectable liquid pouches. It may also be sized to hold multiple flexible pouches secured together in the flexible enclosure. It is to be appreciated that the materials for the component parts of the injection device, including the casing, preferably are non-ferromagnetic so as not to interfere with magnetic resonance imaging devices.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An injection device for injecting medical liquids, the device comprising:

a flexible pouch containing medical liquid, the pouch having an outlet orifice for connection with tubing that is interconnected with an injection needle;

a casing which defines an internal compartment which contains an inert, motive liquid and is connected with a means for pressurizing the motive liquid, the flexible pouch being received within the casino such that pressure from the inert, motive liquid causes a discharge of the medical liquid from the flexible pouch, the casing being symmetrically disposed along a plane of longitudinal symmetry and including:

a casing body having an upper opening disposed at an upper end of the casing body, the casing body having a substantially ovoid shape in transverse section, a movable sealing means which sealing means is movable between an open position in which a passage is defined to receive the flexible pouch and a closed position closing the casing body upper opening and permitting the casing to be pressurized.

2. The injection device as set forth in claim 1 wherein the casing body includes:

a lower end wall;

at least two lateral wall portions of rounded shape connected to the lower end wall and extending toward the upper end.

3. The injection device as set forth in claim 2 wherein the lateral wall portions each have a transverse section defined by a circular arc segment of common radius in the transverse plane, said circular arc segments are non-concentric.

4. The injection device as set forth in claim 3 wherein the radius of the arc segment of the lateral wall portions is constant along a longitudinal length of the casing body.

5. The injection device as set forth in claim 1 wherein the casing further includes:

a deformable enclosure disposed in the interior of the casing body.

6. The injection device as set forth in claim 1 wherein the sealing means includes:

an orifice which permits the connection of the flexible pouch to one of a supply conduit and a discharge tube therethrough.

7. The injection device as set forth in claim 1 wherein the plane of longitudinal symmetry is disposed vertically with the upper opening of the casing body being oriented in an upward direction.

8. An injection device for injecting medical liquids, the device comprising:

a flexible pouch containing medical liquid;

a casing which defines an internal compartment which receives an inert, motive liquid and is connected with a means for pressurizing the motive liquid, the flexible pouch being received within the casing, the casing further including:

a casing body having an upper opening disposed at an upper end of the casing body, a movable sealing means which is movable between an open position to receive the flexible pouch and a sealed position closing the casing and permitting the casing to be pressurized, a deformable enclosure disposed in the interior of the casing body and including:

two planar, flexible walls extending in a longitudinal direction; and a divergent wall defined at an upper end of the two planar flexible walls.

9. The injection device as set forth in claim 8 wherein the deformable enclosure is disposed with the planar flexible walls lying parallel to the plane of longitudinal symmetry.

10. An injection device for injecting medical liquids, the device comprising:

a flexible pouch containing medical liquid;

a casing which defines an internal compartment which contains an inert, motive liquid and is connectable with a means for pressurizing the motive liquid, the casing further including:

a casing body having an opening, a movable sealing means which is movable between an open position to permit the casing body opening to receive the flexible pouch and a sealed position closing the casing body opening and permitting the casing to be pressurized, a deformable enclosure disposed in the interior of the casing body and including:

a shaping means for expanding and shaping the deformable enclosure sufficient to receive the flexible pouch filled with medical liquid.

11. The injection device as set forth in claim 10 wherein the shaping means includes a cage arranged around the deformable enclosure.

12. An injection device for injecting medical liquids, the device comprising:

a flexible pouch containing medical liquid;

a casing which defines an internal compartment which contains an inert, motive liquid and is connected with a means for pressurizing the motive liquid, the flexible pouch being received within the casing, the casing further including:

a casing body having an upper opening disposed at an upper end of the casing body, the casing body having a substantially ovoid shape in transverse section, a cover having two complementary movable parts which open relative to each other to receive the flexible pouch and close relative to each other to permit the casino to be pressurized.

13. An injection apparatus for injecting a medical liquid, the apparatus comprising:

a casing body including:

a pair of curved side wall portions which are symmetric about a longitudinal plane, an end wall connected with the side wall portions for closing one end of the casing body, an opening defined at an opposite end of the side wall portions;

a stopper which is movably connected with the opening at the other end of the side walls for movement between an open position and a closed position, in the closed position, the stopper forms a fluid tight seal with the casing body, the stopper defining a passage therethrough;

a flexible pouch containing medical liquid to be injected, the flexible pouch being connected with a fluid carrying conduit which is adapted for interconnection to a cannula, the flexible pouch being received within the casing body with the tubing being received in a fluid tight seal with the passage through the stopper;

a source of motive fluid for supplying motive fluid under pressure to the casing body such that the motive fluid under pressure urges the flexible pouch to compress, urging the medical liquid through the tubing.

14. The injection apparatus as set forth in claim 13 wherein the stopper includes first and second portions which are pivotally connected to the casing body side walls, each portion of the stopper defining a part of the fluid passage.

15. The injection apparatus as set forth in claim 13 further including a deformable enclosure which is hermetically sealed to said opposite end of the casing body, the deformable enclosure being expandable in an absence of the stopper to define a cavity for receiving the flexible pouch, the deformable enclosure having a collapsed configuration in which it conforms to a shape of the received flexible pouch.

16. The injection apparatus as set forth in claim 15 further including a guide for limiting and defining the open configuration of the deformable en closure.

17. The injection device as set forth in claim 8 wherein the sealing means is shaped in form and dimension to follow the divergent wall of the deformable enclosure.

18. A method of injecting a medical liquid, the method comprising:
  drawing a negative pressure on a motive fluid disposed in an interior of a casing body which is generally oval in transverse cross section, the negative pressure causing a deformable enclosure to expand;
  inserting a flexible pouch that contains the medical liquid and which is connected with a length of flexible tubing into the expanded deformable enclosure;
  passing the tubing through an aperture in a closure for the casing body;
  sealing the closure to the casing body in a fluid tight seal;
  pressurizing the motive fluid in the casing body to squeeze the flexible pouch and force the medical liquid through the tubing;
  injecting the medical liquid that is forced through the tubing into a subject, such that the medical liquid which is forced from the flexible pouch and through the flexible tubing is injected.

19. An injection device for injecting medical liquids, the device comprising:
  a flexible pouch containing medical liquid, the pouch having an inlet orifice for connection with tubing that is interconnected with an injection needle;
  an enclosure which defines an internal compartment which contains an inert, motive liquid and is connected with a means for pressurizing the motive liquid, the flexible pouch being received within the enclosure such that pressure from the inert, motive liquid causes a discharge of the medical liquid from the flexible pouch, the enclosure being symmetrically disposed along a plane of longitudinal symmetry and including:
    a casing body having an upper opening disposed at an upper end of the casing body, the casing body having a substantially oval shape in transverse section,
    a lid which is movable between an open position to receive the flexible pouch and a sealed position to close the upper opening, the lid including:
      an upper plate, that is oval in transverse section,
      a projection extending downward from the upper plate, the projection (i) being oval and (ii) progressively decreasing in transverse section.

* * * * *